Nov. 24, 1953 H. M. TIRET Plant Pat. 1,231
FUCHSIA PLANT
Filed Dec. 22, 1952
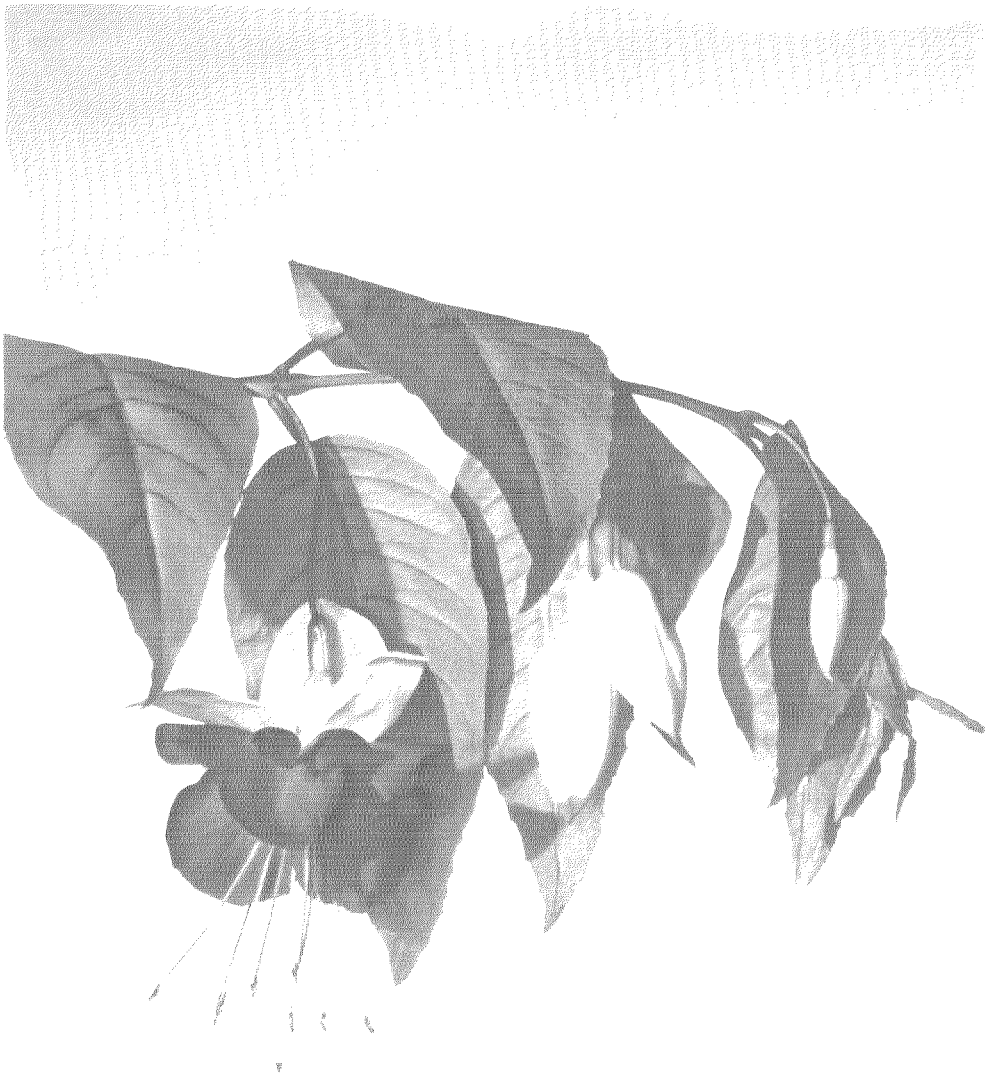
Inventor
Horace M. Tiret Patented Nov. 24, 1953

Plant Pat. 1,231

UNITED STATES PATENT OFFICE 1,231

FUCHSIA PLANT

Horace M. Tiret, San Francisco, Calif.

Application December 22, 1952, Serial No. 327,463

1 Claim. (Cl. 47—60)

This invention relates to a new and improved fuchsia plant, the principal new and different characteristic of which is the sulferino purple color of the petals, the exceptionally large size and the contrasting white sepals.

The plant was derived as a hybrid from seedlings (unpatented) not introduced to the trade, namely 3/18/11 by 3/36/5, the figures representing applicant's own breeding symbols. The fuchsia plant is distinguished principally by its green foliage, vigorous, willowy habit of growth, distinctive sulferino purple coloring and exceptionally large size, which has not previously been found in this combination in any fuchsia plant. The plant has been asexually reproduced at Palo Alto, Santa Clara County, California, by cuttings which retained the characteristics of the parent fuchsia.

The plant is an upright variety and grows vigorously, throwing willowy branches during the process of growth. When the plant blooms, the long, medium broad, waxy white buds, with green tips, open into large double flowers. The bud is waxy white, tinted green at the tip, and the flower is sulferino purple (Horticultural Color Chart 26). The outer petals in some cases have a crimson color (Horticultural Color Chart 22/2) running from the base of the petal outward toward the tip, and shading to the dominant color, sulferino purple. From the base of the large petals a faint streak of white extends from the sepals partially down the center. The flower has no fragrance.

In the accompanying drawing, the figure shows a typical branch tip, including both a bud and fully opened blossom, the drawing representing approximately actual size.

A detailed description of this new variety of fuchsia plant follows:

*Habit of growth.*—Strong, upright variety which throws out willowy branches from the roots and whose branches in turn are self-branching. Flowers occur both along the stem and at the tips of the branches.

*Foliage.*—Large green leaves, smooth surfaced, having serrated edges and evenly spaced along the branch. The leaves are large, long and pointed at the tip. Buds are medium broad and shaped like an acorn. The color is waxy white with faint green shading, and green tips.

*Flower.*—The flower is double and of a large size for the genus. The corolla is loosely formed, with many small, horizontal outer petals, giving a general flaring effect. The flower is strongly resistant to wilting at high atmospheric temperature, but grows equally well in the cooler, coastal climate of the west. The color is sulferino purple (Horticultural Color Chart 26), which is the outstanding, different and distinctive feature of this plant, with the outer petals in some cases having a crimson color (Horticultural Color Chart 22/2), running from the base outward toward the tip.

*Ovary.*—Long, slender, and light green in color.

*Tube.*—Slender, medium long, colored flesh with green tinting.

*Petals.*—From thirteen to eighteen petals occur to each flower, the petals being loosely formed. As the flower matures, the petals retain their loosely formed, flaring effect. The petals are sulferino purple, with a crimson accent occurring in the outer petals on occasion, all as above described.

*Stamens.*—The stamens are long, approximately 1⅝ inches in length, measured from the seed pod, and of a dark pink color, and terminate short of the long pistil, approximately 2¾ inches in length, measured from the seed pod, having a yellow tip which hangs below the cluster of stamens.

*Sepals.*—Long, medium broad, waxy white in color, and smooth textured. The underside of the sepals is waxy white flushed pink.

*Parentage.*—Applicant's own seedlings (unpatented) and not introduced to the trade, applicant's breeding symbols 3/18/11 and 3/36/5.

It is noted that the foliage and flowers will vary somewhat with the seasons and growing conditions; however, the fuchsia plant is clearly differentiated from others by the sulferino purple coloring of the petals, the contrasting waxy white sepals and the exceptionally large size.

Having thus disclosed my discovery I claim:

The new and distinct variety of fuchsia plant herein described and illustrated, characterized by the sulferino purpose coloring of the petals contrasted with the waxy white sepals.

HORACE M. TIRET.

No references cited.